(12) United States Patent
Naya (10) Patent No.: US 7,952,707 B2
(45) Date of Patent: May 31, 2011

(54) MICROSTRUCTURES, METHOD FOR PRODUCING MICROSTRUCTURES, AND OPTICAL FIELD AMPLIFYING DEVICE

(75) Inventor: Masayuki Naya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 317 days.

(21) Appl. No.: 12/134,487

(22) Filed: Jun. 6, 2008

(65) Prior Publication Data

US 2008/0304060 A1    Dec. 11, 2008

(30) Foreign Application Priority Data

Jun. 8, 2007    (JP) .................................. 2007-152824

(51) Int. Cl.
  *G01N 21/65* (2006.01)
  *G01N 21/64* (2006.01)
(52) U.S. Cl. ..... 356/301; 356/317; 250/281; 250/458.1; 436/172
(58) Field of Classification Search .................... 356/301
  See application file for complete search history.

(56) References Cited

U.S. PATENT DOCUMENTS 7,288,419 B2    10/2007    Naya

FOREIGN PATENT DOCUMENTS

| EP | 1016621 A2 | 7/2000 |
|---|---|---|
| EP | 1541994 A1 | 6/2005 |
| EP | 1553400 A1 | 7/2005 |
| EP | 1580305 A2 | 9/2005 |
| EP | 1541994 B1 | 4/2007 |
| JP | 2001-303022 A | 10/2001 |
| JP | 2002-025635 A | 1/2002 |
| JP | 2003268592 A | 9/2003 |
| JP | 2004-530867 A | 10/2004 |
| JP | 2005-259674 A | 9/2005 |
| JP | 2006083450 A | 3/2006 |

OTHER PUBLICATIONS

Extended European Search Report corresponding to European Patent Application No. 08010356 dated Feb. 19, 2010.
Chinese Office Action, dated Jun. 23, 2010, Appln. No. 200810125544.5.

*Primary Examiner* — F. L Evans
(74) *Attorney, Agent, or Firm* — Sughrue Mion, PLLC (57) ABSTRACT

A microstructure is formed on a conductor. The microstructure is equipped with a dielectric base material, in which a great number of fine holes having substantially the same shape in plan view are formed. The fine holes are open at the surface of the dielectric base material, and are substantially uniformly provided therein. A plurality of micro metal members are fixed to the dielectric base material. The micro metal members include filling portions that fill one or more of the fine holes, and protruding portions that protrude from the surface of the dielectric base material and are of diameters greater than the fine holes, capable of inducing local plasmon. The plurality of micro metal members include those that have different numbers of filling portions.

13 Claims, 6 Drawing Sheets

MICROSTRUCTURES, METHOD FOR PRODUCING MICROSTRUCTURES, AND OPTICAL FIELD AMPLIFYING DEVICE

BACKGROUND OF THE INVENTION

1. Field of the Invention

The present invention relates to a microstructure equipped with a dielectric base material having a plurality of fine holes in the surface thereof and metal members capable of inducing local plasmon, a method for producing the microstructure, and an optical field amplifying device that utilizes the microstructure.

2. Description of the Related Art

Light energy transfer elements that efficiently utilize solar energy, are being considered. Solar energy is being investigated as a new, clean, and safe alternative energy source to replace fossil fuels such as oil. The photosynthesis function of plants has been noted as a highly efficient method of light energy transfer, and there is expectation for development of artificial light energy transfer elements (artificial photosynthesis elements) equipped with artificially constructed photosystem complexes that have photosynthesis functions.

Japanese Unexamined Patent Publication Nos. 2001-303022 and 2002-25635 disclose light energy transfer elements (photoelectric conversion systems). These light energy transfer elements are equipped with: a metal or semiconductor base material; and a mixed self assembled monolayer. These light energy transfer elements are easy to produce, and light which is absorbed by the complex can be highly efficiently converted to energy. However, because the film thickness of the monolayer is several nm, the absorption efficiency of incident light is extremely low.

In order to obtain higher efficiency, light energy transfer elements that employ microstructures having electric field amplifying effects on the surfaces thereof as the base material on which the photosystem complexes are provided are being considered. Japanese Unexamined Patent Publication No. 2005-259674 discloses a photoelectric conversion element. In this photoelectric conversion element, photosystem complexes are formed on a microstructure constituted by electrodes which are formed by accumulated gold nanoparticles. The high specific surface area of the gold nanoparticles and an electric field amplifying effect caused by local plasmon enables highly efficient photoelectric conversion of incident light, by photosystem complexes which are immobilized on the electrodes at high density.

PCT Japanese Patent Publication No. 2004-530867 discloses an optical amplifying substance, in which a plurality of agglomerated nanoparticles (including fractals) are provided in the vicinity of microcavities, as a microstructure having an electric field amplifying effect. U.S. Pat. No. 7,288,419 discloses a microstructure equipped with a dielectric base material and a plurality of fine metal particles. In this microstructure, highly densely arranged fine holes are provided in the surface of the dielectric base material, and each of the metal particles includes a filling portion that fills a fine hole, and a head portion that protrudes from the surface of the dielectric base material and which are of a size capable of inducing local plasmon resonance.

However, in the microstructures disclosed by Japanese Unexamined Patent Publication No. 2005-259674 and PCT Japanese Patent Publication No. 2004-530867, the bonds between the metal particles that constitute the photosystem complexes and the base materials are weak. Therefore, the metal particles flake off easily, and it is difficult to stably hold the photosystem complexes. Accordingly, it is difficult to realize uniform function across the entire surfaces of the microstructures.

In the microstructure disclosed by U.S. Pat. No. 7,288,419, the metal particles which are capable of inducing local plasmon are embedded in the base material. Therefore, the metal particles are less likely to flake off than in the structures disclosed by Japanese Unexamined Patent Publication No. 2005-259674 and PCT Japanese Patent Publication No. 2004-530867.

However, it is necessary to form the metal particles such that a single head portion corresponds to each filling portion that fills the fine holes, which are arranged at high density within the surface of the dielectric base material. The process for forming a head portion for each of the plurality of filling portions, which are microstructures on the order of nanometers, is not easy, and there is a possibility that yield will suffer.

SUMMARY OF THE INVENTION

The present invention has been developed in view of the foregoing circumstances. It is an object of the present invention to provide a microstructure that exhibits electric field amplification effects having high planar uniformity and which can be produced by a simple process. The microstructure may be employed as an optical field amplifying device, for a light energy transfer element or the like. It is another object of the present invention to provide a method for manufacturing the microstructure.

It is still another object of the present invention to provide an optical field amplifying device which is equipped with the aforementioned microstructure.

A first microstructure of the present invention comprises:

a dielectric base material having a great number of fine holes which are open at the surface of the base material; and a plurality of micro metal members, each of which have a filling portion that fills one or more of the fine holes and a protruding portion that protrudes from the surface of the base material and is of a diameter greater than the diameter of the filling portion, capable of inducing local plasmon; and is characterized by:

the plurality of micro metal members including those that have different numbers of filling portions that fill different numbers of the fine holes.

In the present specification the term "great number" is defined as a number far greater than the number of fine holes which are filled by the filling portions.

In addition, the "diameter" of the protruding portion is defined as the maximum diameter thereof.

A second microstructure of the present invention comprises:

a dielectric base material having a great number of fine holes which are open at the surface of the base material; and a plurality of micro metal members, each of which have a filling portion that fills one or more of the fine holes and a protruding portion that protrudes from the surface of the base material and is of a diameter greater than the diameter of the filling portion, capable of inducing local plasmon; and is characterized by:

the plurality of micro metal members being those that have the same numbers of filling portions that fill the fine holes.

It is preferable for the average distance between adjacent protruding portions to be 10 nm or less. Here, the term "distance" refers to the distance between the closest portions of separate and adjacent protruding portions.

It is preferable for the distribution of the fine holes within the dielectric base material to be substantially regular.

It is preferable for the dielectric base material to be formed by a metal oxide which is obtained by anodizing at least a portion of a metallic material, and for the fine holes to be formed within the metal oxide during the anodizing process.

The micro metal members may be formed by plating the interiors of the fine holes formed in the dielectric base material until a portion of the plating protrudes from the surface of the dielectric base material.

An optical field amplifying device of the present invention is equipped with the microstructure of the present invention, and is characterized by:

an amplified electric field being generated on the surface of the microstructure due to the electric field amplifying effect of local plasmon, which is induced by light being irradiated on said surface.

A preferred example of the optical field amplifying device of the present invention has a sample placed in contact with an electric field amplification region created by the local plasmon on the surface thereof; and a measuring light beam that enters the sample is emitted as emitted light beams having different physical properties, depending on the sample.

Another preferred example of the optical field amplifying device of the present invention has a sample placed in contact with an electric field amplification region created by the local plasmon on the surface of the optical amplifying device; and Raman scattered light is generated by a measuring light beam of a specific wavelength entering the sample.

Still another preferred example of the optical field amplifying device of the present invention has a target placed in contact with an electric field amplification region created by the local plasmon on the surface of the optical amplifying device; a laser beam is irradiated onto the target; and the portion of the target irradiated by the laser beam is caused to transpire.

Still yet another preferred example of the optical field amplifying device of the present invention has a sample placed in contact with an electric field amplification region created by the local plasmon on the surface of the optical amplifying device; and a measuring light beam is irradiated onto the sample, to desorb a target of mass spectrometry, which is included in the sample, from the surface.

The optical field amplifying device of the present invention may further comprise:

photosystem complexes, constituted by energy donors that absorb optical energy and donates energy, and energy acceptors that receive the energy donated by the energy donors, formed on the surfaces of the protruding portions of the micro metal members; and be characterized by:

an incident light beam of a wavelength which is capable of inducing local plasmon at the protruding portions, and which includes a wavelength which enables absorption of optical energy by the energy donors, being irradiated onto the surface of the optical field amplifying device.

The optical field amplifying device of the present invention may further comprise:

a sensing surface, to which only a specific target substance bonds, formed at an electric field amplification region created by the local plasmon on the surface of the optical field amplifying device; and be characterized by:

the specific target substance being labeled with a fluorescent marker that selectively bonds with the target substance;

a measuring light beam of a wavelength which is capable of inducing local plasmon at the protruding portions, and of an absorption wavelength that causes two photon excited fluorescence emission or multiphoton excited fluorescence emission by the fluorescent marker being irradiated onto the sensing surface; and the optical field amplifying device being employed in sensing that detects the two photon excited fluorescence or the multiphoton excited fluorescence of the fluorescent marker.

A method for producing a microstructure capable of inducing local plasmon on the surface thereof of the present invention comprises the steps of:

preparing a dielectric base material having a great number of fine holes which are open on the surface thereof; and plating the interiors of the fine holes formed in the dielectric base material such that metal fills the interiors of the fine holes; and continuing plating until the metal protrudes from the surface of the dielectric base material at diameters greater than those of the fine holes.

In the microstructure of the present invention, each of the plurality of micro metal members have a filling portion that fills one or more of the fine holes and a protruding portion that protrudes from the surface of the base material. Each of the protruding portions 22 is of a diameter, which is greater than the diameter of the filling portion and capable of inducing local plasmon. Therefore, the head portions can be provided close to each other, and effective electric field amplification functions can be obtained.

In addition, the micro metal members are of structures wherein portions thereof are embedded in the fine holes of the dielectric base material. Therefore, the micro metal members are not likely to flake off from the dielectric base material, and an electric field amplification effect having high planar uniformity is exhibited. Further, the micro metal members include those of which the filling portions fill a plurality of the fine holes. Accordingly, strict control of the production process is obviated, that is, the micro metal members can be produced by a simple process.

In the first microstructure of the present invention, the micro metal members include those that have different numbers of filling portions that fill different numbers of the fine holes. In this case, the sizes of the protruding portions become non uniform. The wavelength at which an electric field amplifying effect due to local plasmon can be obtained varies according to the type of metal and the size thereof. Therefore, the first microstructure of the present invention, in which the sizes of the protruding portions are not uniform, the wavelengths at which the electric field amplification effect can be obtained are broadened, corresponding to the fluctuation in the sizes of the protruding portions.

BEST MODE FOR CARRYING OUT THE INVENTION

First Embodiment of the Microstructure

Figure 1:
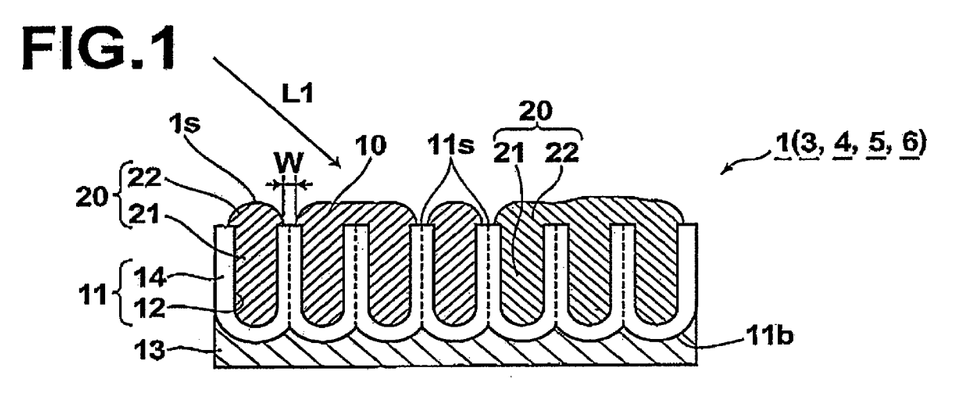
FIG. 1 is a sectional view that illustrates the construction of a microstructure according to a first embodiment of the present invention, taken along the thickness direction thereof.

A microstructure 1 according to a first embodiment of the present invention will be described with reference to the drawings. FIG. 1 is a sectional view that illustrates the construction of the microstructure 1. FIG. 2 and FIG. 3 are diagrams that illustrate the manufacturing steps of the microstructure according to the first embodiment, wherein FIG. 2 shows perspective views of each step, and FIG. 3 shows sectional views of each step.

As illustrated in FIG. 1, the microstructure 1 is formed on a conductor 13, and is equipped with a dielectric base material 11 with a great number of regularly arranged fine holes 12, which are substantially the same shape in plan view, formed such that they are open at the surface 11s of the dielectric base material 11. A plurality of micro metal members 20, each of which have a filling portion 21 that fills one or more of the fine holes 12 and a protruding portion 22 that protrudes from the surface 11s of the base material 11 and is of a diameter, which is greater than the diameter of the filling portion, capable of inducing local plasmon, are fixed to the dielectric base material 11. The plurality of micro metal members 20 include those that have different numbers of filling portions 21 that fill different numbers of the fine holes 12.

An incident light beam L1 that includes wavelengths of light capable of inducing local plasmon at the protruding portions 22 is irradiated onto the surface 11s of the dielectric base material 11 of the microstructure 1. The incident light beam L1 is not particularly limited, and may be natural light, such as sunlight, a light beam emitted by a specific light source, or a broad wavelength band light beam. The incident light beam L1 causes Local plasmon to be induced at the protruding portions 22 of the microstructure 1, and an electric field amplifying effect is obtained due to the local plasmon. The electric field amplification effect due to local plasmon is said to be a hundredfold or greater at the local plasmon resonance wavelength. Accordingly, it is preferable for the incident light beam L1 to include a wavelength of light that causes local plasmon resonance at the protruding portions 22, in order to obtain greater electric field amplification effects.

The fine holes 12 extend substantially straight in the thickness direction of the microstructure 1 from the surface 11s of the dielectric base material 11. The fine holes 12 are closed at the bottom surface 11b of the dielectric base material 11, and do not penetrate therethrough.

In the first embodiment, the dielectric base material 11 is an alumina ($Al_2O_3$) layer 11 (metal oxide layer) which is obtained by partially anodizing a metal material 10 having aluminum (Al) as its main component and which may have slight impurities contained therein, as illustrated in FIG. 2 and FIG. 3. As illustrated in FIG. 2 and FIG. 3, the fine holes 12 are formed as holes having rounded bottoms during the partial anodizing process. The remaining non anodized portion of the metal material 10 becomes the conductor 13.

The shape of the metal material 10 to be anodized is not limited. A metal plate is an example. In addition, the metal material 10 may be formed as a layer on a substrate.

Anodization may be executed by using the metal material 10 as an anode, using carbon, aluminum, or the like as a cathode (opposing electrode), soaking the anode and the cathode in an anodizing electrolytic solution, then applying voltage therebetween. The electrolytic solution is not particularly limited. Acidic electrolytic solutions that include at least one of: sulfuric acid; phosphoric acid; chromic acid; oxalic acid; sulfamic acid; benzene sulfonic acid; amide sulfonic acid; and the like may be favorably employed.

Figure 2A:
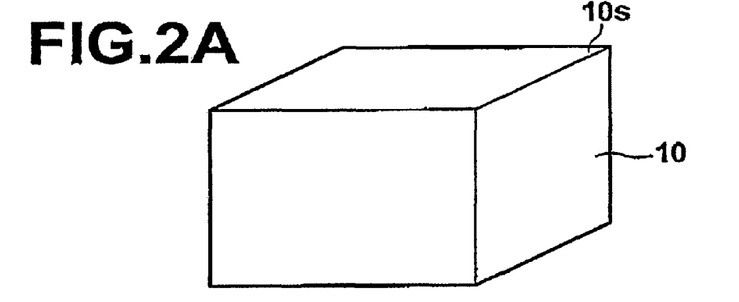
FIG. 2A, FIG. 2B, FIG. 2C, and FIG. 2D are perspective views that illustrate the manufacturing steps of the microstructure according to the first embodiment.
Figure 2B:
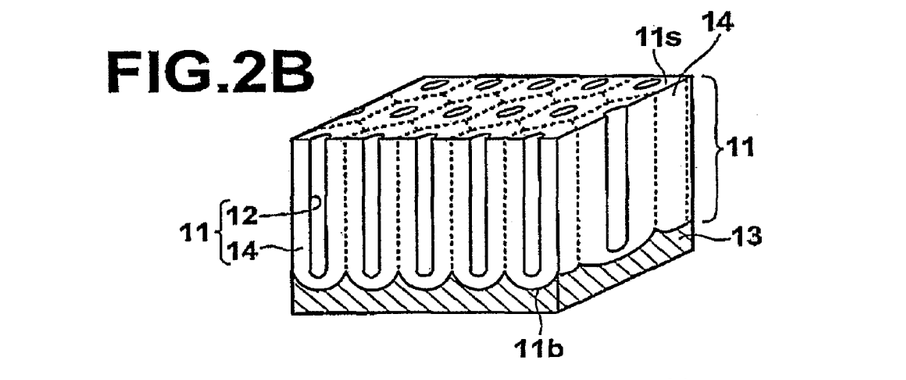
Figure 3A:
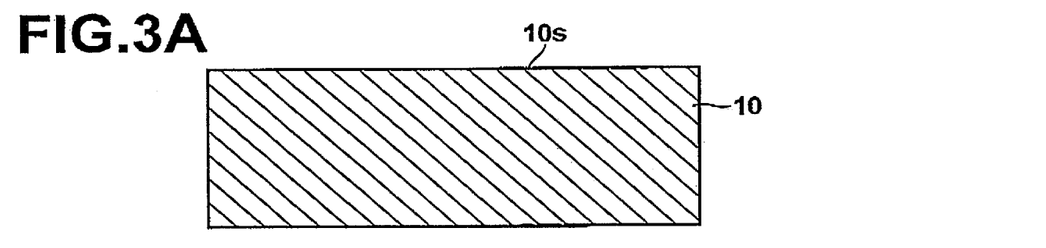
FIG. 3A, FIG. 3B, FIG. 3C, and FIG. 3D are sectional views corresponding to FIG. 2A, FIG. 2B, FIG. 2C, and FIG. 2D, respectively.
Figure 3B:
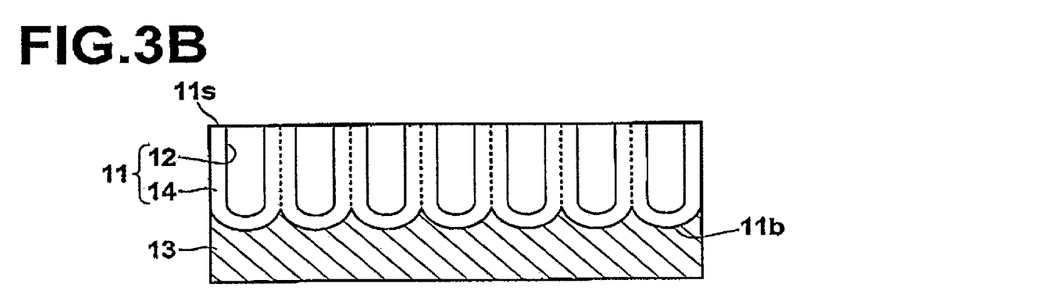

By anodizing the metal material 10 illustrated in FIG. 2A and FIG. 3A, an oxidation reaction progresses substantially in the vertical direction from the surface 10s thereof (the upper surface in the Figures) as illustrated in FIG. 2B and FIG. 3B, to form the alumina layer 11.

The alumina layer 11 formed by anodization is of a structure in which fine columns 14 which are substantially hexagonal in plan view are arranged adjacent to each other. The fine holes 12 that extend in the depth direction from the surface 10s are formed at the approximate centers of each of the fine columns 14. The bottom surfaces of the fine holes 12 and the fine columns 14 are rounded in shape, as illustrated in FIG. 2 and FIG. 3. The structure of alumina layers which are formed by anodization is described in H. Masuda, "Preparation of Mesoporous Alumina and Applications as a Functional Material", Material Science, pp. 34, Vol. 15, No. 10, 1997.

In the first embodiment, partial anodization is performed on the metal material 10. In the case that oxalic acid is employed as the electrolytic solution, an example of favorable anodization conditions are: an electrolytic solution concentration of 0.5M; a solution temperature of 15° C.; and an applied voltage of 40V. By performing anodization under these conditions, the alumina layer 11 (dielectric base material), in which the great number of fine holes 12 of substantially the same shape in plan view and which are open at the surface 11s of the dielectric base material are formed, can be obtained.

Generally, the pitch among adjacent fine holes 12 can be controlled to be within a range of 10 nm to 500 nm. The diameters of the fine holes 12 can be controlled to be within a range of 5 nm to 400 nm. Japanese Unexamined Patent Publication Nos. 2001-9800 and 2001-138300 disclose methods for exerting detailed control on the positions and the diameters of fine holes when forming the fine holes. Fine holes can be regularly arranged and formed with desired diameters and depths within the aforementioned ranges, by employing these methods.

Figure 2C:
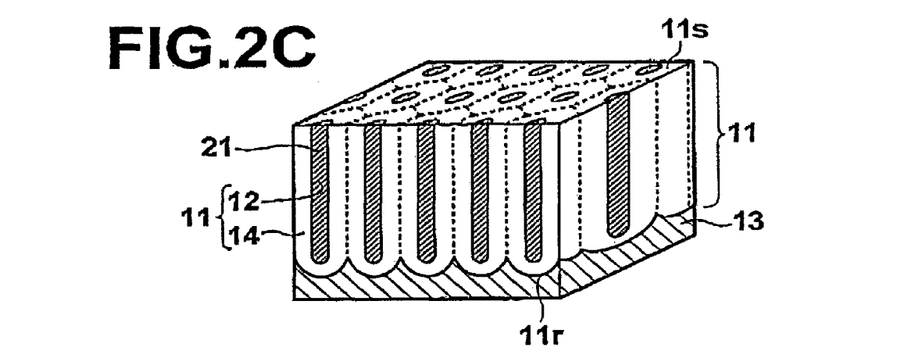
Figure 2D:
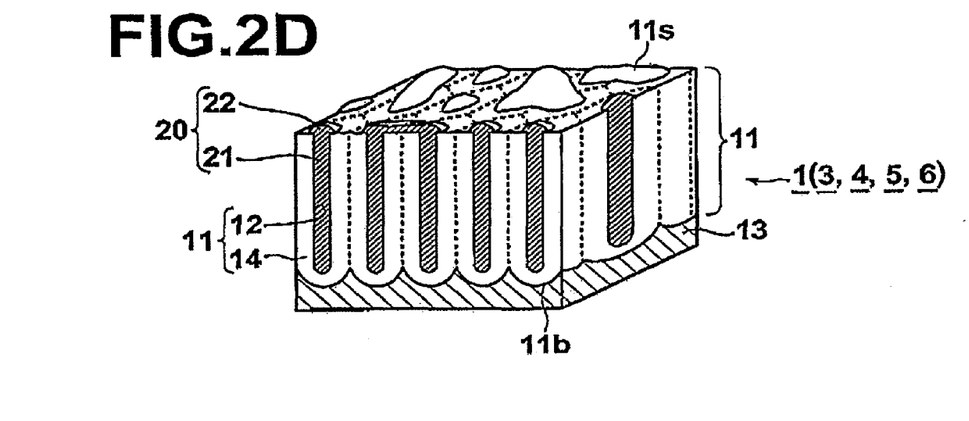
Figure 3C:
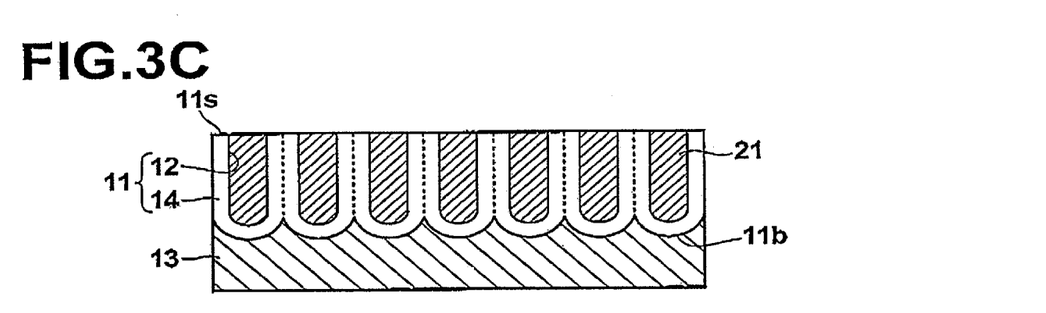
Figure 3D:
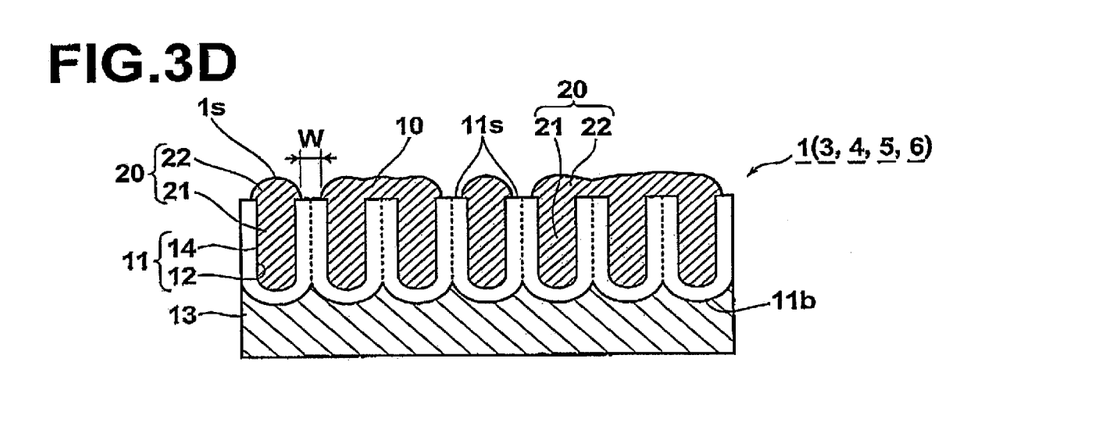

The micro metal members 20, which are constituted by the filling portions 21 and the protruding portions 22, are formed by administering electroplating within the fine holes 12 of the dielectric base material 11, as illustrated in FIG. 2C and FIG. 3C. In this case, the anodized alumina layer 11 is present between the conductor 13 and the bottoms of the fine holes 12. However, by forming the alumina layer 11 at the bottoms of the fine holes 12 sufficiently thin such that conduction is enabled between the conductor 13 and the solution that contains metal within the fine holes 12, electroplating using the conductor 13 as an electrode enables prioritized separation of the metal from the bottoms of the fine holes 12, where electric fields are powerful.

Electroplating using the conductor 13 as an electrode enables prioritized separation of the metal from the bottoms of the fine holes 12, where electric fields are powerful. Therefore, by continuously performing electroplating, the metal fills the interiors of the fine holes 12, to form the filling portions 21 of the micro metal members 20. When electroplating is continued after the filling portions 21 are formed, the metal overflows from the fine holes 12. However, because electric fields are powerful in the vicinities of the fine holes 12, the metal that overflows is isotropically plated at the peripheries of the fine holes 12. The metal which is plated at the peripheries of the fine holes 12 protrude from the surface 11s of the dielectric base material 11 above the filling portions 21, and become the protruding portions 22 which have diameters greater than those of the filling portions 21 (refer to FIG. 2D and FIG. 3D).

The microstructure 1 is equipped with micro metal members 20 having filling portions 21 that fill different numbers of the fine holes 12. The sizes of the protruding portions 22 of the micro metal members 20 change according to the number of fine holes 12 which are filled by the filling portions 21 thereof. For example, in the case that the fine holes 12 which have substantially uniform diameters are arranged substantially regularly, if the number of fine holes 12 filled by the filling portion 21 is doubled, the size of the protruding portion 22 is approximately doubled.

It is necessary to strictly control the plating conditions in order to form the micro metal members 20 such that each filling portion 21 that fills a single fine hole 12 has a single protruding portion 22. The microstructure 1 of the first embodiment is equipped with micro metal members 20 having filling portions 21 that fill different numbers of the fine holes 12. Therefore, it is not necessary to strictly control the plating conditions. Accordingly, the microstructure 1 can be produced by a simple process.

The wavelength at which local plasmon resonance wavelength occurs varies according to the type of metal and the size thereof. Accordingly, if there are fluctuations in the number of fine holes 12 which are filled by the filing portions 21, the sizes of the protruding portions 22 that induce local plasmon also fluctuate. As a result, the wavelengths at which local plasmon can be induced are broadened, corresponding to the fluctuation in the sizes of the protruding portions 22.

In addition, the number of fine holes 12 which are filled by the filling portions 21 can be adjusted by the plating conditions when forming the protruding portions 22. Therefore, the wavelength or the wavelength range at which local plasmon is induced can be varied by changing the plating conditions. If plating is continued after a protruding portion 22 is formed on a filling portion 21 that fills a single fine hole 12, adjacent protruding portions 22 contact each other and become integrated. As a result, single protruding portions 22 which are formed by two protruding portions 22 and micro metal members 22 which are formed by two filling portions 21 that fill two fine holes 12 can be formed. The sizes of the protruding portions 22 can be varied by adjusting the number of protruding portions 22 to be integrated, by the simple process of merely changing the plating conditions.

If the size of the protruding portions 22 is large enough to induce local plasmon, there is no limitation on the number of fine holes 12 which are filled by the filling portions 21. From the viewpoint of broadening the wavelength band at which local plasmon resonance can be induced, it is preferable for the microstructure 1 to include micro metal members 20 having filling portions 21 that fill single fine holes 12. Taking the wavelength and the like of the incident light beam L1 into consideration, it is preferable for the sizes of the protruding portions 22 to be within a range of 10 nm to 300 nm. Protruding portions 22 of sizes within this range are capable of inducing local plasmon with light beams within a wavelength range from 300 nm to near infrared.

It is preferable for adjacent protruding portions 22 to be separated. It is preferable for the average value of distances w among adjacent protruding portions 22 to be within a range of several nm to 10 nm. Electric field amplification effects are known to be particularly powerful when the distance w is 10 nm or less. Accordingly, if the average value of the distances w is within the aforementioned range, an electric field amplification effect due to local plasmon can be effectively obtained.

Local plasmon resonance is a phenomenon in which free electrons within metals resonate with the electric field of light and vibrate, thereby generating strong electric fields in the vicinity of the metals. Therefore, the micro metal members 20 may be any metal that has free electrons. The microstructure 1 induces local plasmon at the protruding portions 22 when the incident light beam L1 is irradiated onto the surface 11s of the dielectric base material. Therefore, metals that generate local plasmon are preferred as materials for the micro metal members 20. Examples of such materials are Au, Ag, Cu, Pt, Ni, and Ti. Au and Ag, which have high electric field amplification effects, are particularly preferable.

Being of the construction described above, the microstructure illustrated in FIG. 2D and FIG. 3D are capable of effectively generating electrical field amplification effects due to local plasmon at the protruding portions 22.

In the microstructure 1, each of the micro metal members 20 have a filling portion 21 that fills one or more of the fine holes 12 and a protruding portion 22 that protrudes from the surface 11s of the dielectric base material 11. Each of the protruding portions 22 is of a diameter, which is greater than the diameter of the filling portions 21 and capable of inducing local plasmon. Therefore, the head portions can be provided close to each other, and effective electric field amplification functions can be obtained.

In addition, the micro metal members 20 are of structures wherein portions thereof are embedded in the fine holes 12 of the dielectric base material 11. Therefore, the micro metal members 20 are not likely to flake off from the dielectric base material 11, and an electric field amplification effect having high planar uniformity is exhibited. Further, the micro metal members 20 include those of which the filling portions 21 fill a plurality of the fine holes 12. Accordingly, strict control of the production process is obviated, that is, the micro metal members 20 can be produced by a simple process.

In the microstructure 1, the micro metal members 20 include those that have different numbers of filling portions 21 that fill different numbers of the fine holes 12. In this case, the sizes of the protruding portions 22 become non uniform. The wavelength at which an electric field amplifying effect due to local plasmon can be obtained varies according to the type of metal and the size thereof. Therefore, the microstructure 1, in which the sizes of the protruding portions 22 are not uniform, the wavelengths at which the electric field amplification effect can be obtained are broadened, corresponding to the fluctuation in the sizes of the protruding portions 22.

Second Embodiment of the Microstructure

Figures 4, 5:
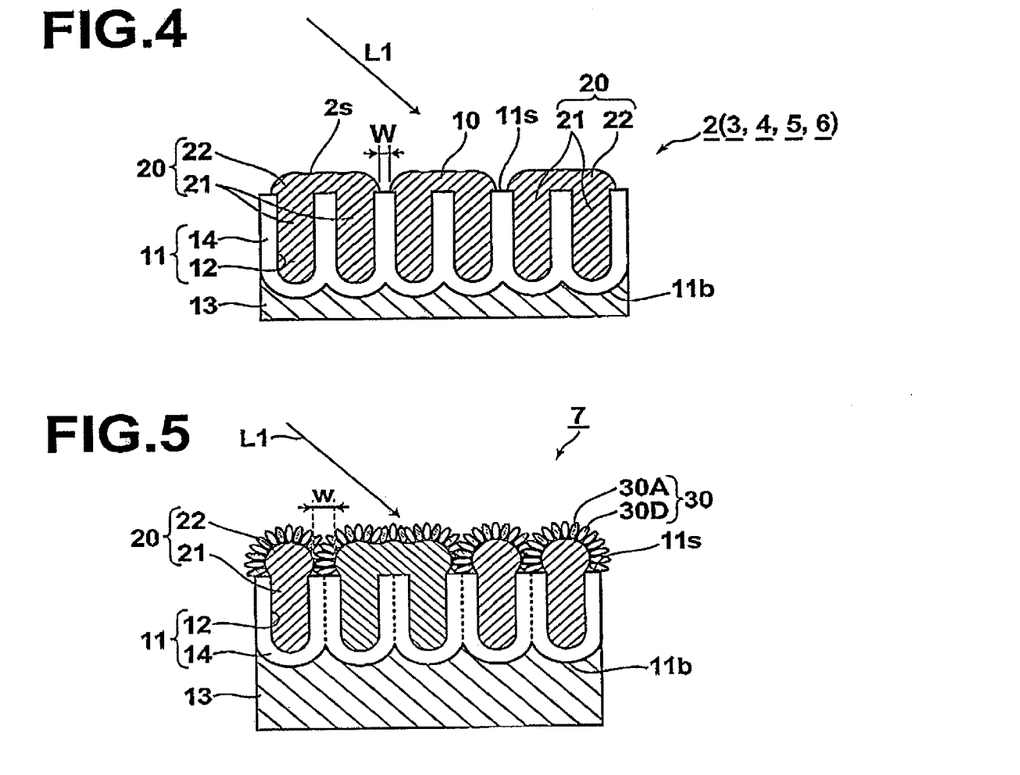
FIG. 4 is a sectional view that illustrates the construction of a microstructure according to a second embodiment of the present invention, taken along the thickness direction thereof.
FIG. 5 is a sectional view that illustrates the construction of a light energy transfer element, which is a preferred embodiment of the optical field amplifying device of the present invention, taken along the thickness direction thereof.

A microstructure 2 according to a second embodiment of the present invention will be described with reference to the drawings. FIG. 4 is a sectional view that illustrates the construction of the microstructure 2.

As illustrated in FIG. 4, the microstructure 2 is formed on a conductor 13, and is equipped with a dielectric base material 11 with a great number of regularly arranged fine holes 12, which are substantially the same shape in plan view, formed such that they are open at the surface 11s of the dielectric base material 11. A plurality of micro metal members 20, each of which have a filling portion 21 that fills one or more of the fine holes 12 and a protruding portion 22 that protrudes from the surface 11s of the base material 11 and is of a diameter, which is greater than the diameter of the filling portion, capable of inducing local plasmon, are fixed to the dielectric base material 11. In the second embodiment, the plurality of micro metal members 20 are those that have the same numbers of filling portions 21 that fill the same numbers of the fine holes 12.

The micro metal members 20 of the microstructure 1 of the first embodiment had different numbers of filling portions 21 that fill different numbers of the fine holes 12. In contrast, the microstructure 2 of the second embodiment differs in that the plurality of micro metal members 20 are those that have the same numbers of filling portions 21 that fill the same numbers of the fine holes 12. That is, there are fluctuations in the sizes of the protruding portions 22 in the first embodiment, whereas the sizes of the protruding portions 22 are substantially uniform in the microstructure 2 of the second embodiment.

Accordingly, the microstructure 2 can be produced in the same manner as the microstructure 1 of the first embodiment, except that the micro metal members 20 are formed under conditions such that the number of fine holes 12 filled by the filling portions become equal. In addition, preferred materials for the microstructure 2 are the same as those for the microstructure 1 of the first embodiment.

In the microstructure 2, the micro metal members 20 each have a filling portion 21 that fills two or more fine holes 12, and a protruding portion 22 that protrudes from the surface 11s of the base material 11 and is of a diameter, which is greater than the diameter of the filling portion 21, capable of inducing local plasmon.

In this structure, the filling portions 21 may be those that fill pluralities of the fine holes 12. Therefore, strict control of plating conditions is not necessary, compared to a structure in which a single protruding portion 22 corresponds to each filling portion 21 that fills the fine holes 12, which are microstructures on the order of nanometers.

As described above, the microstructure 2 differs from the microstructure 1 of the first embodiment in that the sizes of the protruding portions 22 are substantially uniform. Therefore, the effects obtained due to the fluctuations of the sizes of the protruding portions 22 described in the first embodiment are not exhibited. However, because the structures are similar except for the point of uniformity in the sizes of the protruding portions 22, similar advantageous effects can be obtained.

In the second embodiment, the wavelength at which local plasmon resonance is induced can be shifted to longer wavelengths, by increasing the number of fine holes 12 which are filled by the filling portions 21, thereby increasing the sizes of the protruding portions 22. The sizes of the protruding portions 22 vary according to plating conditions. Therefore, for example, in the case that electric field amplification effects are desired at longer wavelengths of incident light, the wavelength at which local plasmon resonance is induced can be shifted to longer wavelengths by a simple design choice of just changing the plating conditions.

[Optical Field Amplifying Device]

The construction of optical field amplifying devices according to embodiments of the present invention will be described with reference to the drawings. As illustrated in FIG. 1 and FIGS. 4 through 6, optical field amplifying devices 3 through 8 are equipped with the microstructure of the present invention. These embodiments will be described as being equipped with the microstructure 1, but the microstructure 2 may similarly be applied.

Local plasmon resonance occurs at the surfaces of the protruding portions 22 of the micro metal members at the surface is of the microstructure 1. The drawings are magnified to facilitate visual representations, and therefore the protrusions and recesses formed by the protruding portions 22 appear to be prominent. However, because the actual dimensions are on the order of nanometers, the protrusions and recesses are small, and the plurality of protruding portions 22 constitute the surface 1s of the microstructure 1. Accordingly, the microstructure 1 generates an amplified electric field by the electric field amplification effect due to local plasmon resonance, when local plasmon resonance is induced by light irradiated onto the surface 1s thereof. The microstructure 1 can be applied favorably as an optical field amplifying device or as a base material for an optical field amplifying device.

The optical field amplifying device of the present invention is equipped with the microstructure 1, and generates an amplified electric field on the surface 1s of the microstructure 1 when light is irradiated on the surface 1s. Examples of optical field amplifying devices include: those that amplify the energy of light to be detected to improve detection sensitivity; those that perform sensing by utilizing changes of the optical properties of emitted light beams; and those that utilize the energy of incident light beams, which have been amplified by the electric filed amplifying effect.

A Raman spectroscopy device 3, in which a sample is placed in contact with an electric field amplification region created by the local plasmon on the surface 1s of the microstructure 1; and Raman scattered light is generated by a measuring light beam L1 of a specific wavelength entering the sample, is an example of an optical field amplifying device that amplifies the energy of light to be detected to improve detection sensitivity. This type of Raman spectroscopy device may be employed in surface enhanced Raman detection, for detecting Raman scattered light, which is amplified by the electric field amplification effect, thereby improving detection sensitivity.

A sensor device 4, in which a sample is placed in contact with an electric field amplification region created by the local plasmon on the surface 1s of the microstructure 1; and a measuring light beam L1 that enters the sample is emitted as emitted light beams having different physical properties, depending on the sample, is an example of an optical field amplifying device that performs sensing by utilizing changes of the optical properties of emitted light beams. For example, in the case of a local plasmon sensor, a specific wavelength of a measuring light beam L1 is absorbed by the electric field amplification effect of local plasmon resonance induced thereby, and is emitted as a light beam having specific absorption properties. Sensing can be performed by detecting changes in the absorption properties, such as shifting in the peak absorbed wavelength, prior to and following contact of the sample.

An ablation device 5, in which a target is placed in contact with an electric field amplification region created by the local plasmon on the surface 1s of the microstructure 1; an incident light beam L1 is irradiated onto the target; and the portion of the target irradiated by the laser beam is caused to transpire, is an example of an optical field amplifying device that utilizes the energy of incident light beams, which have been amplified by the electric filed amplifying effect. Another example of an optical field amplifying device that utilizes the energy of incident light beams which have been amplified by the electric filed amplifying effect is a mass spectroscopy device 6, in which a sample is placed in contact with an electric field amplification region created by local plasmon on the surface 1s of the microstructure 1; and a measuring light beam L1 is irradiated onto the sample, to desorb a target S of mass spectrometry, which is included in the sample, from the surface 1s. In these devices, the energy of the incident light beam L1, which has been amplified by the electric field amplifying effect, is used to cause an irradiated portion of a target to transpire or to desorb the target S of mass spectroscopy. Therefore, the energy of the incident light beam L1 can be reduced.

Another example of an optical field amplifying device that utilizes the energy of incident light beams which have been amplified by the electric filed amplifying effect is a light energy transfer element 7 (refer to FIG. 5), in which photosystem complexes 30, constituted by energy donors 30D that absorb optical energy and donates energy, and energy acceptors 30A that receive the energy donated by the energy donors, are formed on the surfaces of the protruding portions 22 of the micro metal members 20; and wherein: an incident light beam L1 of a wavelength which is capable of inducing local plasmon at the protruding portions 22, and which includes a wavelength which enables absorption of optical energy by the energy donors 30D, is irradiated onto the surface 1s of the microstructure 1. The microstructure 1 can obtain electric field amplification effects at the protruding portions 22. Therefore, the energy of the incident light beam L1 is amplified at the protruding portions 22, the light absorption efficiency of the photosystem complexes 30 is increased, and light energy transfer efficiency (photoelectric conversion efficiency) can be obtained. Further, the micro metal members 20 on which the photosystem complexes 30 are formed are embedded within the dielectric base material 11. Therefore, the photosystem complexes 30 are stably held on the device, and the possibility that planar uniformity will decrease due to the photosystem complexes 30 flaking off is low. Light energy transfer elements are employed as artificial photosynthesis elements such as hydrogen generating elements, and as photovoltaic cells. The light energy transfer element 7 is capable of providing highly efficient artificial photosynthesis elements and photovoltaic cells.

Still another example of an optical field amplifying device that utilizes the energy of incident light beams which have been amplified by the electric filed amplifying effect is a sensor device 8 (refer to FIG. 6), in which a sensing surface, to which only a specific target substance R bonds, is formed at an electric field amplification region created by the local plasmon on the surface 1s of the microstructure 1; and wherein: the specific target substance R is labeled with a fluorescent marker Lu; and a measuring light beam L1 of a wavelength which is capable of inducing local plasmon at the protruding portions 22, and of an absorption wavelength that causes two photon excited fluorescence emission or multiphoton excited fluorescence emission by the fluorescent marker Lu is irradiated onto the sensing surface, which is employed in sensing that detects the two photon excited fluorescence or the multiphoton excited fluorescence of the fluorescent marker Lu.

Figure 6:
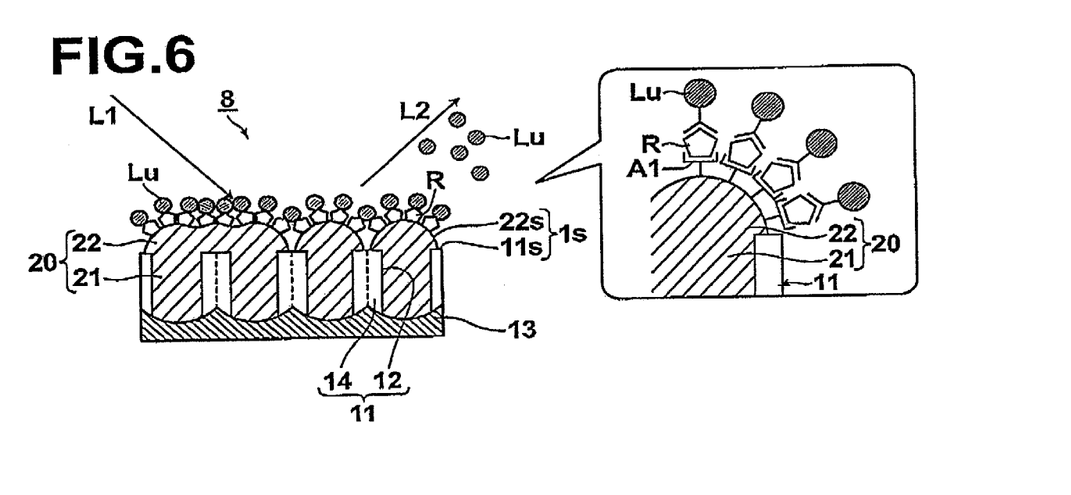
FIG. 6 is a sectional view that illustrates the construction of a two photon fluorescence excitation sensor, which is a preferred embodiment of the optical field amplifying device of the present invention, taken along the thickness direction thereof.

The cross sectional absorption area of two photon excitation and multiphoton excitation is smaller than that of single photon excitation by an order of several powers of ten. Therefore, an expensive high energy light source had been necessary to obtain sufficient fluorescence emission. However, the microstructure 1 can obtain an effective electric field amplification effect at the protruding portions 22. Therefore, remarkable improvements in transition probability can be obtained by the energy of the measuring light beam L1, which is amplified by the electric field amplification effect. Accordingly, the light source can be a low energy light source.

<Design Modifications>

In the above embodiments, the micro metal members 20 are formed by administering plating to the interiors of the fine holes 12. However, the method by which the micro metal members 20 are produced and the method by which the fine holes 12 are filled are not limited to a plating process.

In the above embodiments, the conductor 13 is the non anodized portion of the metal material 10. However, the conductor 13 may be constituted by metal which is provided on the bottom surface 11b of the dielectric base material 11 by vapor deposition or the like. In this case, the material for the conductor 13 is not limited, and conductive materials, such as metals and ITO (Indium Tin Oxide) may be employed.

The above embodiments have been described as cases in which the fine holes 12 do not penetrate through the dielectric base material 11. Alternatively, the dielectric base material 11 may have fine apertures 12 that penetrate therethrough formed therein. The method by which the fine apertures 12 are formed is not limited. Examples include: completely anodizing the metal material 10; and partially anodizing the metal material 10, then removing portions of the dielectric base material 11 from the side of the bottom surface 11b thereof.

The above embodiments have been described as cases in which the conductor 13 is provided on the bottom surface 11b of the dielectric base material 11. However, in the case that conductivity of the fine holes 12 is not required, unlike the case in which electroplating is performed to fill the fine holes 12 with the filling portions 21 of the micro metal members 20, the conductor 13 is not necessary.

Alternatively, the conductor 13 may be removed after the micro metal members 20 are formed.

In the above embodiments, Al was described as being the main component of the metal material 10 which is employed to produce the dielectric base material 11. However, any desired metal maybe used, as long as anodization thereof is possible. Examples of such metals include; Ti, Ta, Hf, Zr, Si, In, and Zn. The metal material 10 may include two or more types of anodizable metals.

The pattern of the fine holes 12 in plan view changes according to the type of metal material 10 which is used. However, The dielectric base material 11 will still have fine holes 12 which are of substantially the same shape in plan view, and which are arranged adjacent to each other.

Cases have been described in which anodization is utilized to arrange the fine holes 12 in a regular manner. However, the method by which the fine holes 12 are formed is not limited to anodization. Anodization is preferable because it is capable of handing large areas and does not require costly equipment. Other examples of microprocessing methods by which the fine holes 12 may be formed include: forming a plurality of regularly arranged recesses in the surface of a resin substrate by a nano imprinting method; and forming a plurality of regularly arranged recesses in the surface of a metal substrate by an electron lithography technique that uses a focused ion beam (FIB), an electron beam (EB) or the like.

It is preferable for the sizes and arrangement of the fine holes 12 within the dielectric base material 11 to be substantially regular, because adjustments to conditions during formation of the micro metal members 20 is facilitated in this case. However, it is not necessary for the sizes and arrangement of the fine holes 12 to be substantially regular.

EXAMPLES

Examples of the present invention and comparative examples will be described.

Example 1

The microstructure 1 of the first embodiment was produced by the following steps.

An aluminum plate (99.99% pure Al, at a thickness of 10 nm) was prepared as the metal material 10 to be anodized. The aluminum plate was used as an anode, and aluminum was used as a cathode, and anodization was performed under conditions that would result in a portion of the aluminum plate becoming an alumina layer 30. Thereby, the dielectric base material 11 and the conductor 13, which is a portion of the metal material 10 that was not anodized, were obtained. Anodization was performed according to the two step anodizing process disclosed in H. Masuda and M. Sato, "Fabrication of Gold Nanodot Array Using Anodic Porous Alumina as an Evaporation Mask", J. J. Appl. Phys. Vol. 35, pp. L126-L129 (1996). The anodizing conditions were the same as those described in this document.

Next, the great number of fine holes 12 within the dielectric base material 11 were filled with Au by plating, using the conductor 13 as an electrode, to form the micro metal members 20. Thus, a microstructure (Raman spectroscopy device) was obtained. The plating process was conducted using a 40 mM tetrachloroauric acid solution, with an applied voltage of 12V at one second cycles with a duty ratio of 0.1 for 10 minutes.

Figure 7A:
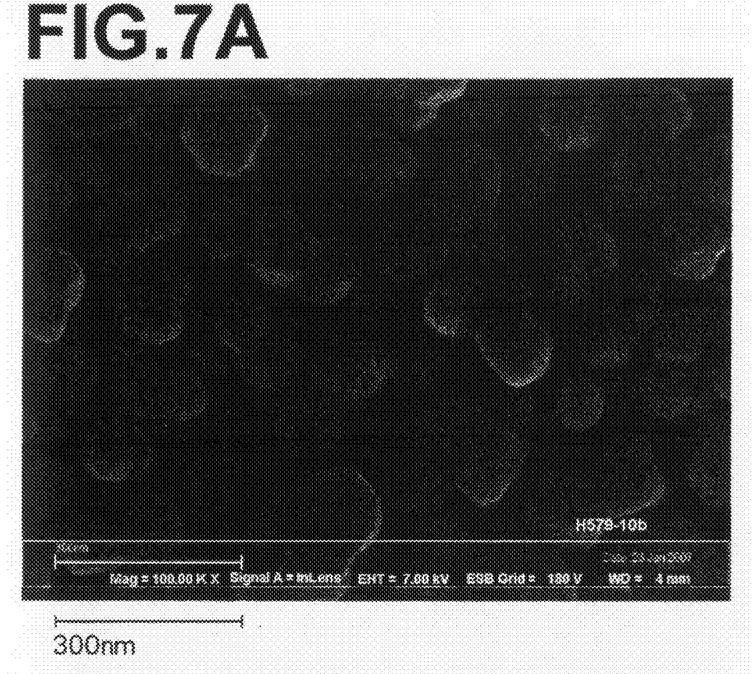
FIG. 7A is a sectional SEM photograph of the microstructure (Raman spectroscopy device) of the first embodiment taken along the thickness direction thereof.
Figure 7B:
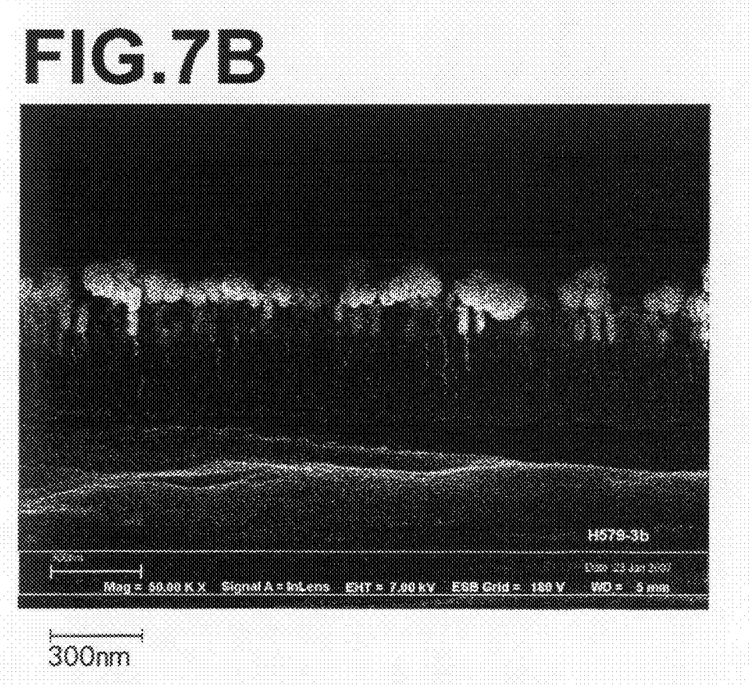
FIG. 7B is an SEM photograph of the surface of the microstructure of the first embodiment.

The results of observing the cross section and the surface of the obtained microstructure (Raman spectroscopy device) with a scanning electron microscope are illustrated in FIG. 7A and FIG. 7B. Although measurement regarding the exact size of the microstructure is difficult from FIG. 7A and FIG. 7B, it was confirmed that the microstructure has a great number of protruding portions having diameters within a range of 60 nm to 200 nm on its surface was confirmed.

Comparative Examples 1 and 2

Au was deposited on glass substrates by vacuum vapor deposition, to form island structured films, which are said to have surface enhancing Raman effects. For comparative example 1, vapor deposition was performed under conditions such that the entire surface of the glass substrate is covered by Au, and such that the thickness of the film is 10 nm, to form a comparative Raman spectroscopy device. For comparative example 2, an annealing process was administered on the glass substrate having the 10 nm thick island structured film on the surface thereof at a temperature of 50° C. for five minutes, to form another comparative Raman spectroscopy device.

(Evaluation)

The same sample fluid was caused to adhere to each of the Raman spectroscopy devices, and the Raman spectra were measured using "HT800" by Horiba Co.

A laser having an oscillation wavelength of 785 nm was used as a light source, and measurements were performed with equal laser power for all three examples. A 150 L/mm spectroscopic detector was used as a spectroscopic means. The sample fluid was a rhodamine 6G (R6G) solution which was diluted to several mM. R6G is known to have a Raman spectral peak at 1360 $cm^{-1}$.

Figure 8A:
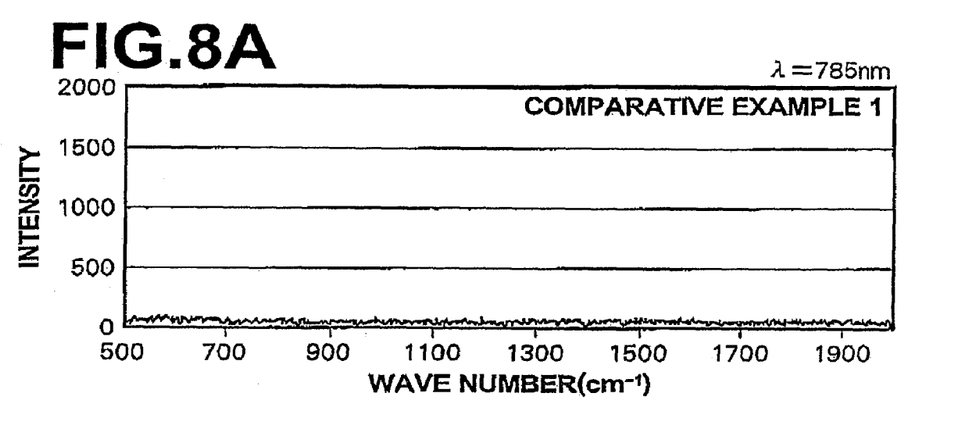
FIG. 8A is a graph that illustrates the Raman spectrum of a first comparative example.
Figure 8B:
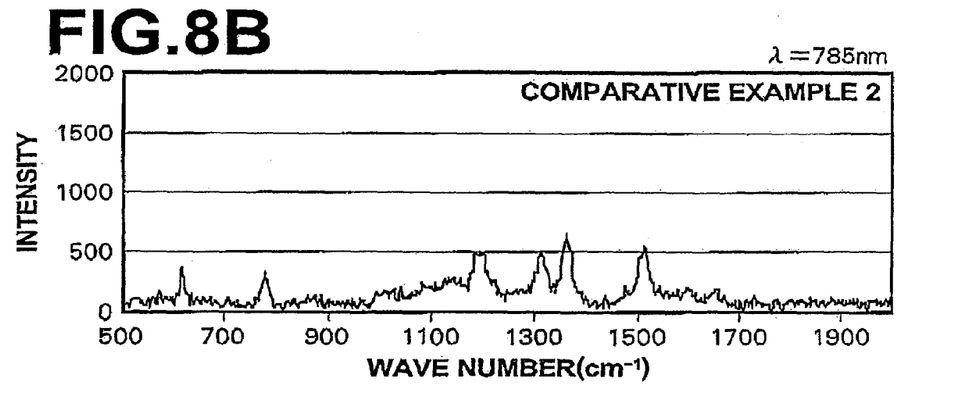
FIG. 8B is a graph that illustrates the Raman spectrum of a second comparative example.
Figure 8C:
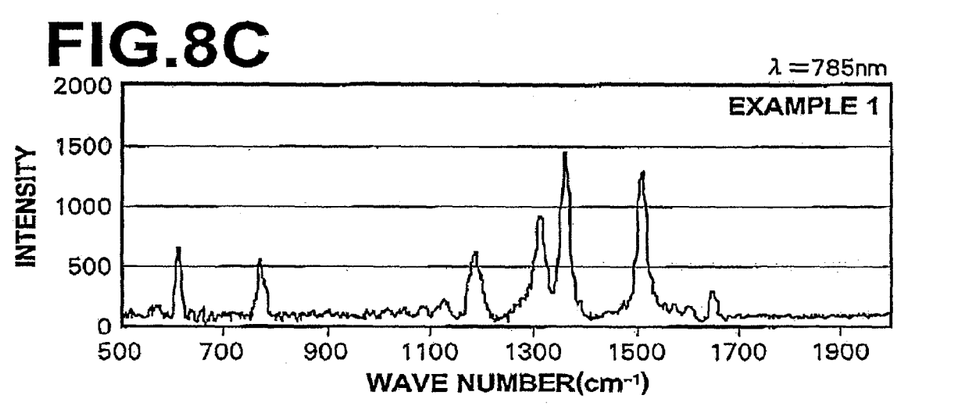
FIG. 8C is a graph that illustrates the Raman spectrum of an Example of the present invention.

The Raman spectrum obtained by each example is illustrated in FIGS. 8A through 8C, respectively. In the figures, the vertical axes of the graphs represent intensity at 500 (a.u.) per tick mark. The Raman spectroscopy device of Example 1 has stronger amplified signals within the range of 500 $cm^{-1}$ to 1700 $cm^{-1}$ over the comparative examples 1 and 2, thereby proving the effectiveness of the present invention.

FIELD OF INDUSTRIAL APPLICATION

The microstructure of the present invention can be favorably utilized as a sensor device used in biosensors, a Raman spectroscopy device, a mass spectrometry device, an ablation substrate, and as a light energy transfer element.

What is claimed is:

1. A microstructure, comprising:
   a dielectric base material having a great number of fine holes which are open at the surface of the base material; and
   a plurality of micro metal members, each of which have a filling portion that fills one or more of the fine holes and a protruding portion that protrudes from the surface of the base material and is of a diameter, which is greater than the diameter of the filling portion, capable of inducing local plasmon; wherein:
   the plurality of micro metal members include those that have filling portions that fill different numbers of the fine holes.

2. A microstructure as defined in claim 1, wherein:
   the micro metal members include those that have one filling portion that fills a single fine hole.

3. A microstructure as defined in claim 1, wherein:
   the average distance between adjacent protruding portions is 10 nm or less.

4. A microstructure as defined in claim 1, wherein:
   the distribution of the fine holes within the dielectric base material is substantially regular.

5. A microstructure as defined in claim 1, wherein:
   the dielectric base material is formed by a metal oxide which is obtained by anodizing at least a portion of a metallic material; and
   the fine holes are formed within the metal oxide during the anodizing process.

6. A microstructure as defined in claim 1, wherein:
   the micro metal members are formed by plating the interiors of the fine holes formed in the dielectric base material until a portion of the plating protrudes from the surface of the dielectric base material.

7. An optical field amplifying device, comprising:
   a dielectric base material having a great number of fine holes which are open at the surface of the base material; and
   a plurality of micro metal members, each of which have a filling portion that fills one or more of the fine holes and a protruding portion that protrudes from the surface of the base material and is of a diameter, which is greater than the diameter of the filling portion, capable of inducing local plasmon; wherein:
   the plurality of micro metal members include those that have filling portions that fill different numbers of the fine holes; and
   an amplified electric field is generated on the surface of the optical field amplifying device due to the electric field amplifying effect of local plasmon, which is induced by light being irradiated on said surface.

8. An optical field amplifying device as defined in claim 7, wherein:
   a sample is placed in contact with an electric field amplification region created by the local plasmon on the surface of the optical field amplifying device; and
   a measuring light beam that enters the sample is emitted as emitted light beams having different physical properties, depending on the sample.

9. An optical field amplifying device as defined in claim 7, wherein:
   a sample is placed in contact with an electric field amplification region created by the local plasmon on the surface of the optical amplifying device; and
   Raman scattered light is generated by a measuring light beam of a specific wavelength entering the sample.

10. An optical field amplifying device as defined in claim 7, wherein:
    a target is placed in contact with an electric field amplification region created by the local plasmon on the surface of the optical amplifying device;
    a laser beam is irradiated onto the target; and
    the portion of the target irradiated by the laser beam is caused to transpire.

11. An optical field amplifying device as defined in claim 7, wherein:
    a sample is placed in contact with an electric field amplification region created by the local plasmon on the surface of the optical amplifying device; and
    a measuring light beam is irradiated onto the sample, to desorb a target of mass spectrometry, which is included in the sample, from the surface.

12. An optical field amplifying device as defined in claim 7, further comprising:
    photosystem complexes, constituted by energy donors that absorb optical energy and donates energy, and energy acceptors that receive the energy donated by the energy donors, formed on the surfaces of the protruding portions of the micro metal members; and wherein:
    an incident light beam of a wavelength which is capable of inducing local plasmon at the protruding portions, and which includes a wavelength which enables absorption of optical energy by the energy donors, is irradiated onto the surface of the optical field amplifying device.

13. An optical field amplifying device as defined in claim 7, further comprising:
    a sensing surface, to which only a specific target substance bonds, formed at an electric field amplification region created by the local plasmon on the surface of the optical field amplifying device; and wherein:
    the specific target substance is labeled with a fluorescent marker that selectively bonds with the target substance;
    a measuring light beam of a wavelength which is capable of inducing local plasmon at the protruding portions, and of an absorption wavelength that causes two photon excited fluorescence emission or multiphoton excited fluorescence emission by the fluorescent marker is irradiated onto the sensing surface; and
    the optical field amplifying device is employed in sensing that detects the two photon excited fluorescence or the multiphoton excited fluorescence of the fluorescent marker.

* * * * *